United States Patent [19]
Romanus

[11] Patent Number: 5,188,133
[45] Date of Patent: Feb. 23, 1993

[54] DENTAL FLOSSING TOOL

[76] Inventor: Thomas W. Romanus, 14804 Werris Creek La., San Diego, Calif. 92128

[21] Appl. No.: 832,232

[22] Filed: Feb. 7, 1992

[51] Int. Cl.⁵ ............................................. A61C 15/00
[52] U.S. Cl. .................................. 132/325; 132/322; 132/326; 132/327
[58] Field of Search ............... 132/322, 324, 325, 326, 132/327

[56] References Cited

U.S. PATENT DOCUMENTS

| | | | |
|---|---|---|---|
| 1,102,401 | 7/1914 | Gamble | 132/325 |
| 1,445,009 | 2/1923 | Eby | 132/325 |
| 3,667,483 | 6/1972 | McCabe | 132/322 |
| 3,789,859 | 2/1974 | Chambers | 132/326 |
| 4,307,740 | 12/1981 | Florindez et al. | 132/322 |
| 4,706,695 | 11/1987 | Urso | 132/322 |

OTHER PUBLICATIONS

"Oral Hygiene Products and Practice", Pader, Morton, *The Toothbrush and Other Mechanical Devices*, 1988, pp. 179–194.

"Evaluation of a Floss-Holding Device Compared to Hand-Held Floss for Interproximal Plaque, Gingivitis, and Patient Acceptance", Kleber, Carl J. et al., *Clinical Preventive Dentistry*, vol 10, No. 4, 1988, pp. 6–14.

"Formation of Flossing Habit Using a Floss-Holding Device", Kleber, Carl J. et al., 1990, pp. 140–143.

*Primary Examiner*—John J. Wilson
*Attorney, Agent, or Firm*—Brown, Martin Haller & McClain

[57] ABSTRACT

The dental flossing device comprises an elongated cylinder, at least a portion of which is hollow, with an extension having a forked end with curved prongs. A commercially-available spool of floss is located on a spindle in the hollow portion of the cylinder. A first locking mechanism holds the floss in a small space between two surfaces with sufficient friction to firmly retain the floss. When relaxed, the floss can be readily pulled through the first locking mechanism. The floss is fed to the exterior where it is stretched across fork prongs. The floss is threaded through a second locking mechanism similar to the first. The two locking mechanisms are controlled by a single external control and, thus, are both activated or deactivated at the same time. They oppose each other, pulling different points on the floss to create and maintain a strong tension in the floss where it spans the fork, thus facilitating flossing. An alternate embodiment has a removable disposable extension and forks for use by dental professionals. A floss spool is contained within the disposable portion of the device as well as an uptake spool. Floss is advanced by an electrically-powered motor.

13 Claims, 3 Drawing Sheets

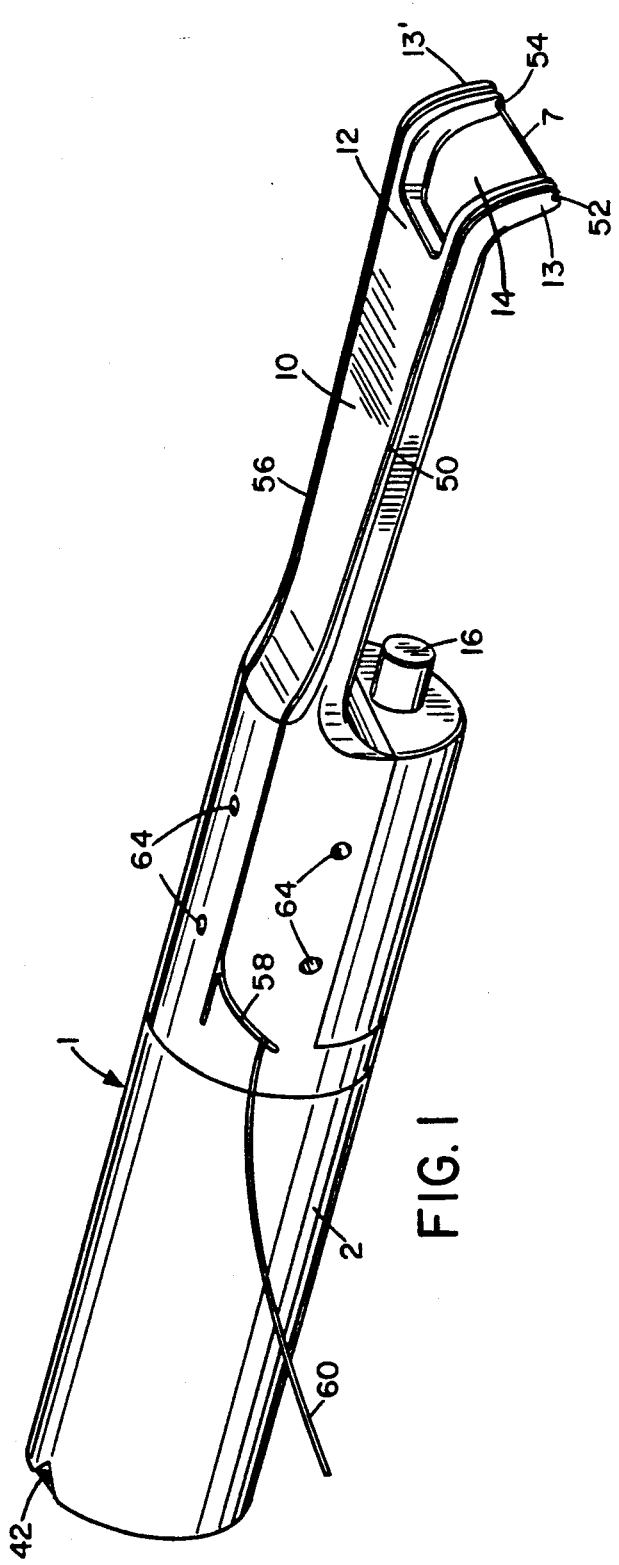
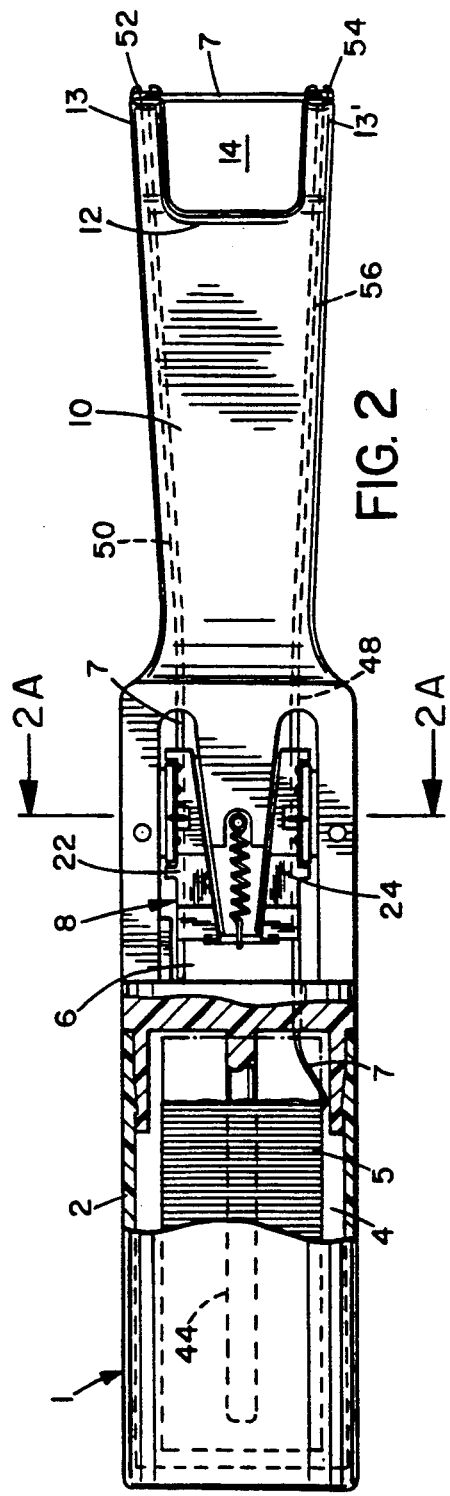

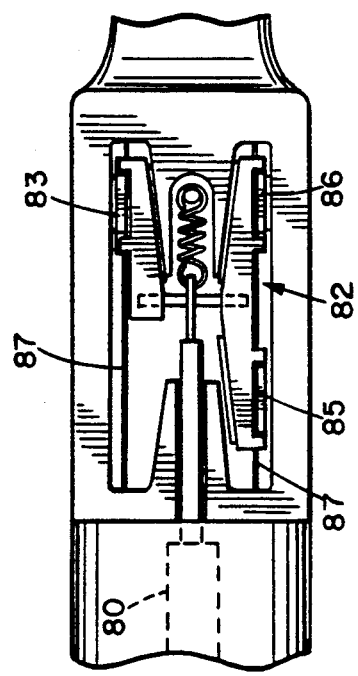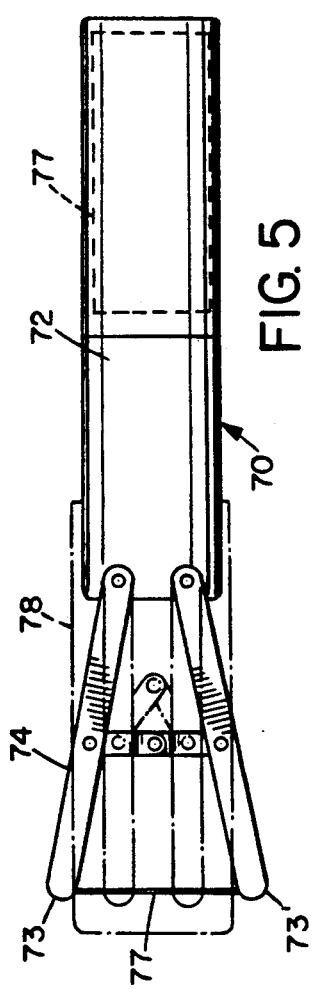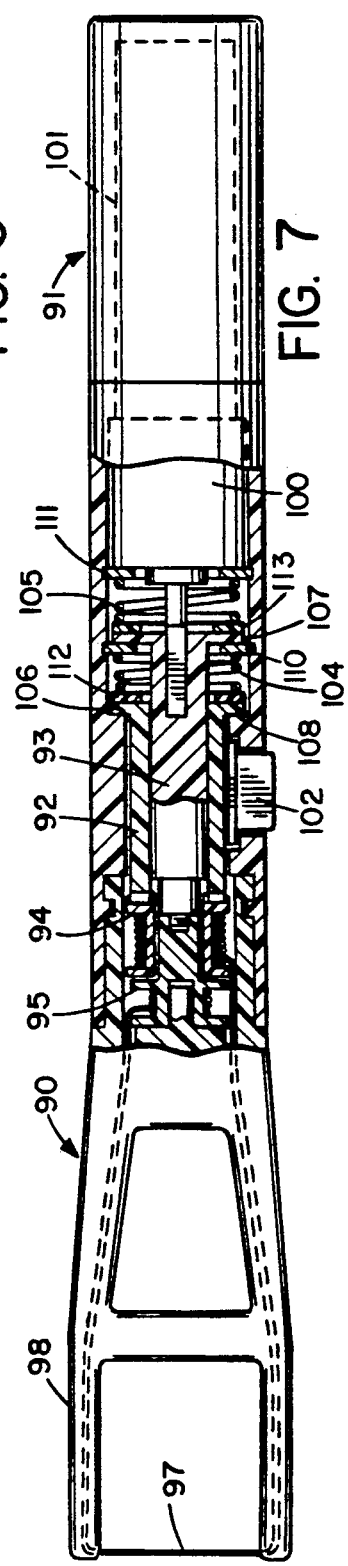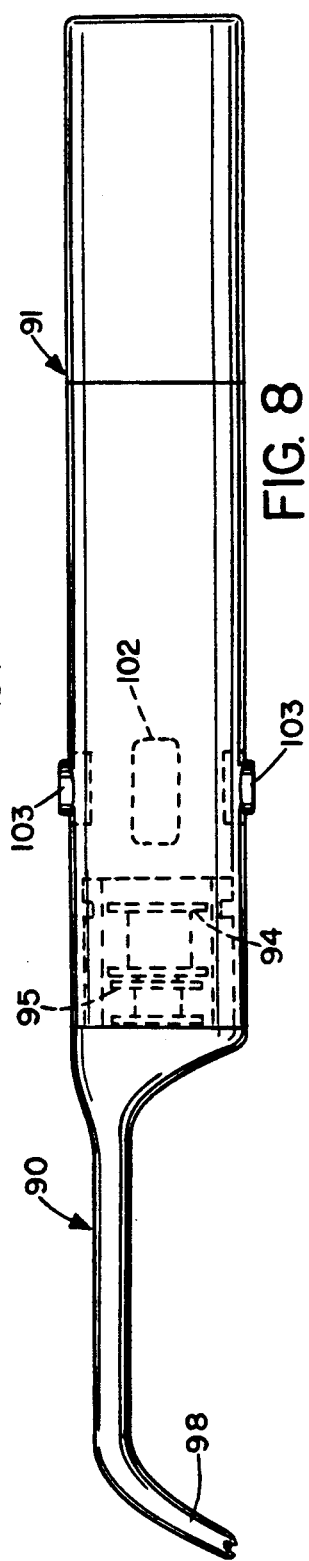

DENTAL FLOSSING TOOL

BACKGROUND OF THE INVENTION

Advances in dental and chemical technology have provided toothpastes, mouth rinses and cleaning instruments which prevent a substantial portion of the tooth decay which in the past resulted in tooth loss. With this success, dentists and manufacturers of oral hygiene products have now directed their focus toward prevention of gum disease which also is a significant cause of tooth loss. One of the oldest yet still most effective means to combat gum disease is flossing.

In recent years, dentists and dental hygienists have placed a great deal of emphasis on the importance of regular flossing, preferably on a daily basis. Flossing has been shown to be highly effective in removing interproximal plaque and reducing gingivitis, however, only the most conscientious individuals maintain a daily regimen of flossing. Flossing is often unpleasant and has a number of problems which ultimately result in the failure to floss daily. Flossing can cause gagging and it can be painful trying to hold one's mouth open long enough and wide enough to floss every tooth. Also, it is difficult to work with fingers from both hands in the mouth so that the force applied to get the floss between the teeth can be excessive so that the floss snaps into the gum causing it to bleed, it can be painful wrapping the floss tight enough around the fingers to maintain the needed tension, and it is unpleasant having to handle the wet, used floss. In addition, while floss is relatively inexpensive, so much floss is used in a single cleaning, on the order of one-and-a-half to two feet, that a lot of floss is used and disposed of in a relatively short time. This waste will be particularly significant when flossing is done daily as it should be. At a time when disposability is not always a positive feature due to environmental concerns, the amount of floss disposed of should ideally be minimized.

A number of flossing devices are currently commercially available which have the object in mind of avoiding use of an individual's fingers to position the floss appropriately. These devices, however, are constructed of inexpensive plastics and the forks which stretch the floss bend under strain so that the tension is decreased and inconsistent. Also, many of these devices are configured so that they must be held in an awkward manner, practically placing the fingers in the mouth just to control the placement. Clearly, these devices have not become widely accepted because they have not resulted in the increased regularity of flossing among the general populace. Also, dental hygienists continue to clean their patients' teeth with the floss wrapped around their fingers rather than using a tool, although this is partly due to the fact that hygienists are trained to floss in this manner.

With the above limitations of the current technology in mind, it would be desirable to provide an economical flossing device which maintains the appropriate tension, is easy to manipulate within the mouth, is comfortable to hold, is conservative in its use of floss, and is suitable for use by both individuals for themselves and dental professionals for their patients. It is toward this goal that the present invention is directed.

SUMMARY OF THE INVENTION

In an exemplary embodiment, the dental flossing device comprises an elongated cylinder, at least a portion of which is hollow, with an extension having a forked end with curved prongs. A commercially-available spool of floss is located on a spindle in the hollow portion of the cylinder. The floss is partially unwound to provide a leading end which is threaded through a first locking mechanism which, in its normal state, holds the floss in a small space between two surfaces with sufficient friction to firmly retain the floss. When relaxed, the floss can be readily pulled through the first locking mechanism. The floss is fed through a channel in the cylinder to its exterior where it rests in a groove in the extension running up to one of the fork prongs, across to the other prong, then back down the extension in another groove. A second channel allows the floss to be fed back into the cylinder's interior where it is threaded through a second locking mechanism similar to the first, then out of the cylinder through an exhaust channel and groove. The two locking mechanisms are controlled by a single external control and, thus, are both activated or deactivated at the same time. Because they oppose each other, pulling different points on the floss, they create and maintain a strong tension in the floss where it spans the fork, thus facilitating flossing.

The floss is advanced by pulling on its exhaust end while engaging the external control to deactivate the locking mechanisms. A recessed blade is placed in the cylinder end to permit the exhausted floss to be cut. The spool at the feed end automatically unwinds to provide the desired length of floss. Once used up, the spool can be replaced with another.

An alternate embodiment has a removable disposable extension and forks for use by dental professionals. A floss spool is contained within the disposable portion of the device as well as an uptake spool. Floss is advanced by an electrically-powered motor, e.g., battery driven, from which a drive shaft extends to be connected to the spool cores. The handle is made of a material which is sturdy and can be readily cleaned and sterilized, such as stainless steel.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which:

FIG. 1 is a perspective view of a first embodiment of the present invention;

FIG. 2 is an underside view, partially cut away, of the first embodiment;

FIG. 5 is a top view of a second embodiment;

FIG. 6 is a view of the locking mechanism of a third embodiment;

FIG. 7 is an underside view, partially cut away, of a fourth embodiment; and

FIG. 8 is a side view partially cut away, of the fourth embodiment.

DETAILED DESCRIPTION OF THE PREFERRED EMBODIMENTS

Figure 2A:
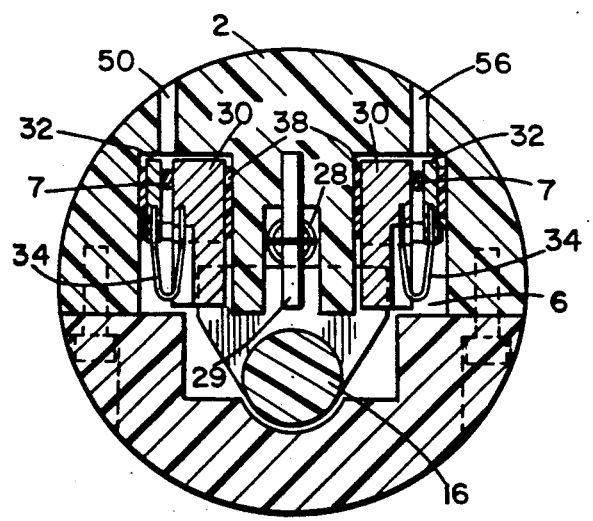
FIG. 2A is an enlarged sectional view taken on line 2A—2A of FIG. 2 and rotated 90°.

As illustrated in FIGS. 1, 2 and 2A, the dental flossing device 1 comprises a cylindrical handle 2 which has a hollow interior, providing cavity 4 in which a spool 5 of floss 7 is placed and cavity 6 in which locking mechanism 8 is located. Extension 10 guides the floss 7 up to fork 12 where the floss 7 is stretched across the space 14 between the prongs 13 and 13' of fork 12. Locking mechanism 8 is spring-loaded and can be deactivated by a trigger 16 or lever on the exterior of the handle 2.

Figure 3:
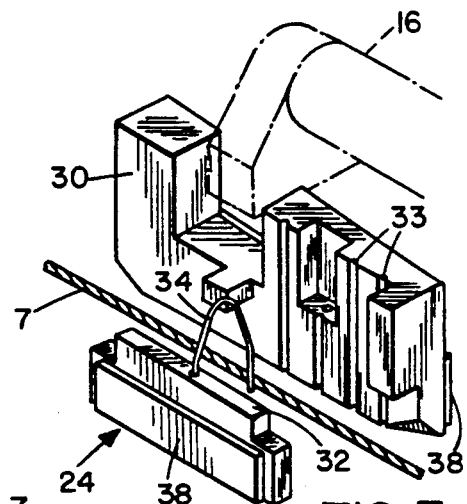
FIG. 3 is an exploded perspective view of a set of plates of a locking mechanism.
Figure 4A:
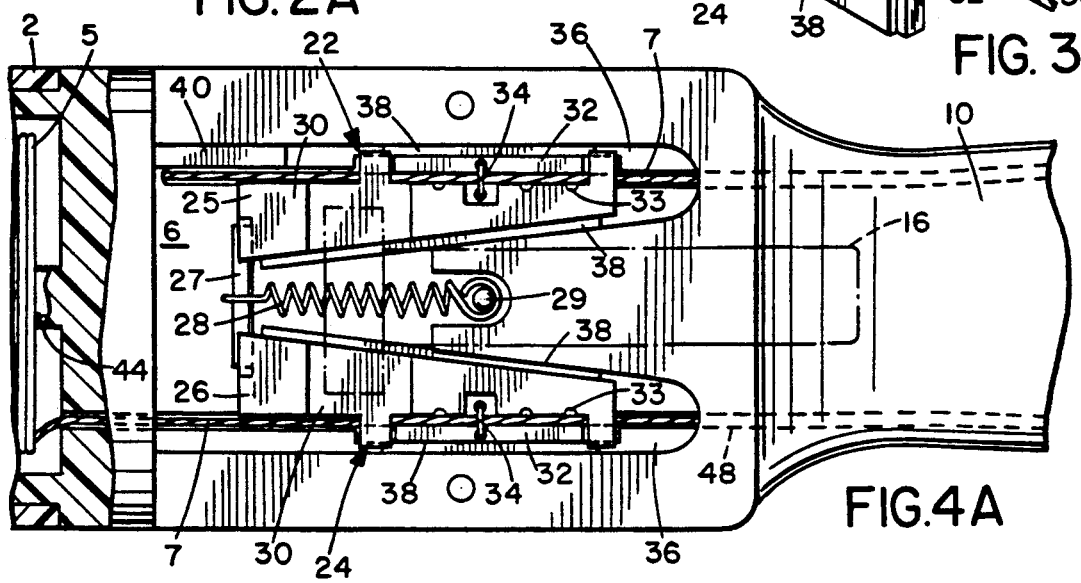
FIGS. 4a and 4b are detailed views of the locking mechanism with FIG. 4a showing the locked position and FIG. 4b showing the released position.
Figure 4B:
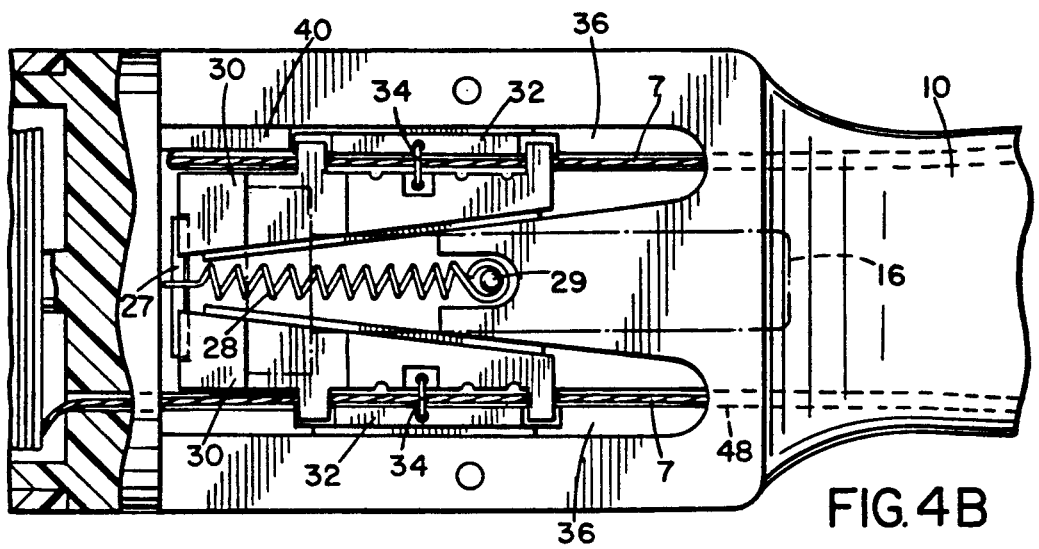

Locking mechanism 8, illustrated in detail in FIGS. 3 and 4, is made of two sets of plates, feed set 22 and exhaust set 24, which are mirror images of each other. Sets 22 and 24 are joined at their bases 25 and 26 by bar 27 and are deactivated simultaneously by depressing trigger 16, causing trigger extension 16' to simultaneously slide sets 22 and 24 backward, toward the wider ends of the wedge-shaped channels. A spring 28 is affixed to bar 27 and stationary pin 29 to provide tension by which the locking mechanism 8 remains locked until deactivated. Alternately, a compression spring, leaf spring or any other type of spring may be utilized to maintain the locking mechanism 8 in the locked position until it is deactivated on command. The spring 28 is attached to stationary pin 29 and bar 27, as shown in FIGS. 2A, 4A and 4B, in such a manner that a slight offset can occur between bases 25 and 26. As illustrated, the end loops of spring 28 are loosely fitted to permit motion, either pivoting or rotation, around pin 29 or bar 27, or the spring itself can extend at an angle slightly off of a straight backward direction. While release of the feed set 22 and the exhaust set 24 are simultaneous as a result of trigger extension 16' pressing on the two sets simultaneously, it is possible for a slight offset between bases 25 and 26 to occur when the locking mechanism 8 is in the locked position by pulling the end of the floss 7. The friction between the floss 7 and interlocking plates 30 and 32 pulls the set of plates backward a very minute distance, which is just enough to release the compression between the plates to allow the floss 7 to move in the direction of the pulling force. This is what permits ready adjustment of the tension on the floss. Where other types of springs are used, the same flexibility will occur because they can be compressed at a slight angle from the straight backward direction.

Since sets 22 and 24 are mirror images of each other, description of one set will apply to the other. Set 22 consists of two interlocking plates 30 and 32 which are connected by a spring 34 which provides a bias forcing the two plates apart. A hairpin-like spring is illustrated, but a leaf spring or other type of spring can be similarly used. Set 22 is in the form of a wedge which moves within wedge-shaped channel 36 of cavity 6. The farther set 22 is toward the narrow end of channel 36, the more compression is supplied to press plates 30 and 32 together. Floss 7 is locked in place when set 22 is compressed. In order to assure sufficient hold is generated, one or both inner surfaces of plates 30 and 32 may have grooves 33 running transverse to the direction of the floss 7. The sides of plates 30 and 32 which contact the walls of channel 36 are coated with a lubricant or other low friction coating to minimize friction and assure smooth travel. In the exemplary embodiment, a coating 38 of Teflon ® or other self-lubricating polymer is used.

A stop 40 is provided within cavity 6 to limit the travel of sets 22 and 24 during deactivation of the locking mechanism 8.

Trigger 16 deactivates locking mechanism 8 by pulling sets 22 and 24 away from the narrowest end of channel 36, thereby allowing the plates 30 and 32 to separate sufficiently to allow the floss to slide between them. The function of trigger 16 can be achieved by depressing a button, as illustrated, or by a lever, slide or any similar element.

At the base of handle 2 a blade 42 is provided to allow used floss to be removed. Blade 42 is preferably recessed so that a person using the flossing device could not inadvertently cut themself while holding the handle.

The chamber 4 in which spool 5 is retained is openable so that an empty spool can be replaced. A spindle 44 is provided around which spool 5 rotates when the free end of the floss 7 is pulled. Cavity 4 can be accessed by a removable cap which snaps, screws or otherwise attaches to the rest of the body of the device 1, or can be a sliding door in the side or end of the cylinder.

After the floss 7 is unwound from spool 5 it is fed from cavity 4 into cavity 6 where it is threaded between plates 30 and 32 of set 22. The floss 7 passes through opening 48 to the exterior of handle 2 and lies inside groove 50 which cuts longitudinally through handle 2 and runs along the top of extension 10 to the end of prong 13. By pulling floss 7 down into groove 50 it can be threaded between plates 30 and 32 of set 22 by deactivating the locking mechanism. A small groove 52 is cut perpendicular to groove 50 across the end of prong 13 to guide the floss 7 across space 14 to groove 54 in prong 13'. Floss 7 then travels back down prong 13' and extension 10, guided by groove 56. Groove 56 continues into the handle 2 where it cuts through the wall to access cavity 6 and locking mechanism 8. Pulling floss 7 directly across groove 56 and into angled groove 58 allows it to be threaded between plates 30 and 32 of set 24 when the locking mechanism 8 is deactivated. Upon release of trigger 16, set 24 will grasp floss 7, holding it in place. The leading end 60 of floss 7 can be pulled downward toward the end of handle 2 to provide the desired tension for flossing.

In order to clean or rinse the device, flushing ports 64 may be made through the handle walls to run water or antiseptic solution through and to drain the cavities.

The materials of which the flossing device 1 is made may include moldable plastics, nylon, polyester or other polymers. The locking mechanism 8 can be aluminum, stainless steel or various plastics or polymers—including the springs.

In a first alternate embodiment, a folding travel version 70 of the flossing device can be made as illustrated in FIG. 5. The handle 72 is smaller and more streamlined, holding a smaller amount of floss 77. The fork 74 is hinged so that the prongs 73 and 73' can be closed together or opened and locked for use. This embodiment may include a cap 78 which fits over fork 74 in its closed position and snaps onto handle 72 for attachment.

A second alternate embodiment for which the locking mechanism is illustrated in FIG. 6 uses an electrically-driven mechanism to advance the floss 87 and maintain the desired tension. The locking mechanism 82 is similar to that of the first embodiment but may include three sets of plates, 83 on the load side, and 85 and 86 on the exhaust side. When the drive mechanism 80 is activated the load set 83 moves backward and releases the floss 87 while set 86 tensions the floss. Simultaneously, exhaust set 86 releases the floss 87 while set 85 tightens the floss as the floss moves backward. When drive mechanism 80 is deactivated, load sets 83 and 86 return forward, providing the necessary floss tension, and exhaust set 85 moves forward, to its original position with set 85 locking on the floss 87. Other mechanisms may be utilized to advance floss while maintaining tension on the floss. A similar configuration to the multiple sets for this embodiment can be used to make a manually controlled device automatically advance the floss by activation of a trigger.

In a third alternate embodiment illustrated in FIGS. 7 and 8, a disposable attachment 90 connects with a handle 91 in which an electrical drive mechanism consisting of an electric drive motor 100 and battery 101. Battery 101 may be rechargeable. Concentric drive shafts 92 and 93 extend from drive motor 100 to be inserted through the cores of feed spool 94 and uptake spool 95, respectively, within attachment 90. The drive shafts each have teeth which interlock with teeth on the spools so that slippage does not occur. The feed spool 94 nests over a portion of the uptake spool 95 so that both are centered on a common axis with the drive shafts. Drive shaft 92 drives the rotation of feed spool 94, providing tension adjustment means by way of a tension setting button 102 to vary the drag of the outer drive shaft 92 on inner drive shaft 93. Inner drive shaft 93 attaches directly between drive motor 100 and uptake spool 94. When the drive motor 100 is activated by pressing floss advance buttons 103 (one on each side of the handle), drive shaft 93 is rotated, causing both spools to turn. The drive assembly also includes springs 104 and 105 which provide tension against flanges 106 and 107 of drive shafts 92 and 93, respectively, pushing them away from drive motor 100. The travel of the drive shafts 92 and 93 due to springs 104 and 105 is limited by a narrowing of the inner diameter of the handle at point 108. Springs 104 and 105 do not rotate with the draft shafts, but are held in place by snap rings 110 and 111 which are inserted into channels in the inner diameter of the handle 91. Washers 112 and 113 are provided for lubrication and smooth rotation of the drive shafts against the springs. The floss 97 is prethreaded across fork 98 so that attachment 90 can simply be snapped onto handle 91, possibly by use of a pin/snap-lock type assembly, and used. Such a configuration is ideal for use by dental professionals, where a disposable attachment 90 can be used for each patient. The handle 91 would be made of a material which is sturdy and is easily cleaned and sterilized, such as stainless steel. The attachment 90 can be made from molded plastic or polymer and could be available in individual, sterilized packages for quick installation.

It will be apparent that various combinations of the elements of each embodiment can be made to produce an effective flossing device. It is also evident that various packaging techniques can be utilized to make the device more attractive, e.g., designing a scaled-down device as an animal or cartoon character for a child's use. These and other variations are considered to be within the scope of the invention.

It will be evident that there are additional embodiments which are not illustrated above but which are clearly within the scope and spirit of the present invention. The above description and drawings are therefore intended to be exemplary only and the scope of the invention is to be limited solely by the appended claims.

I claim:

1. A dental cleaning device to facilitate the insertion of floss between a pair of teeth comprising:
    a handle comprising an elongated and substantially hollow body;
    a forked extension extending from said handle having a pair of prongs and grooves for guiding said floss to span a space between said pair of prongs;
    a first releasable locking mechanism to inhibit a first motion of said floss away from a floss source and to allow said floss to advance away from said floss source when feeding is desired;
    a second releasable locking mechanism to inhibit a second motion of said floss toward a floss exhaust and to allow said floss to advance toward said floss exhaust when exhausting is desired;
    a joining means for releasably joining said first releasable locking mechanism and said second releasable locking mechanism, said joining means permitting partially independent movement and release of said first and second releasable locking mechanisms; and
    wherein said floss is stretched across said pair of prongs with sufficient tension to insert said floss between said pair of teeth.

2. A dental cleaning device as in claim 1 wherein said forked extension is removable from said handle.

3. A dental cleaning device as in claim 1 wherein an electric drive motor is disposed within said handle.

4. A dental cleaning device as in claim 3 wherein said first releasable locking mechanism includes a feed spool providing said floss source.

5. A dental cleaning device as in claim 3 wherein said second releasable locking mechanism includes an uptake spool providing said floss exhaust.

6. A dental cleaning device as in claim 1 wherein said floss source is a spool of floss removably disposed within said handle.

7. A dental cleaning device as in claim 1 wherein said first releasable locking mechanism and said second releasable locking mechanism each comprise a pair of plates between which said floss is sandwiched, said pair of plates pressing together to retain said floss.

8. A dental cleaning device as in claim 1 wherein said first releasable locking mechanism and said second releasable locking mechanism each comprise two pair of plates between which said floss is sandwiched wherein a first pair of plates is a feed set and a second pair of plates is a locking set.

9. A dental cleaning device as in claim 8 wherein said first releasable locking mechanism and said second releasable locking mechanism are driven by an electric drive motor wherein said feed set of said first releasable locking mechanism is activated substantially simultaneously with said feed set of said second releasable locking mechanism.

10. A dental cleaning device comprising:
    a handle comprising an elongated and substantially hollow body;
    a spool of floss rotatably disposed within said handle;
    a forked extension extending from said handle having a pair of prongs and a pair of parallel grooves for guiding floss fed from said spool up one side of said extension and down a second side of said extension so that said floss spans said pair of prongs;

a first locking mechanism for providing a first resisting motion to resist said floss being pulled away from said spool;

a second locking mechanism for providing a second resisting motion to resist said floss being pulled back toward said first locking mechanism;

a release mechanism for simultaneously releasing said first locking mechanism and said second locking mechanism; and a joining means for releasably joining said first locking mechanism and said second locking mechanism, said joining means permitting partially independent movement and release of said first and second locking mechanisms;

wherein said floss is stretched across said pair of prongs with sufficient tension to permit flossing.

11. A dental cleaning apparatus as in claim 10 wherein said spool of floss is removable and replaceable.

12. A dental cleaning apparatus as in claim 10 wherein said first locking mechanism and said second locking mechanism each comprise a pair of plates between which said floss is disposed which press together to retain said floss.

13. A dental cleaning apparatus as in claim 10 wherein said first locking mechanism and said second locking mechanism each comprise two pair of plates between which said floss is disposed wherein a first pair of plates is a feed set and a second pair of plates is a locking set.

* * * * *